(12) United States Patent
Chen et al.

(10) Patent No.: US 7,770,582 B2
(45) Date of Patent: Aug. 10, 2010

(54) REMOVABLE TONGUE POSITION CORRECTIVE ANTI-SNORING AND ANTI-SUFFOCATING DEVICE

(75) Inventors: Haidong Chen, Shanghai (CN); Yueyang Chen, Shanghai (CN)

(73) Assignee: Shanghai Guang Ren Anti-Snoring Health Center, Shanghai (CN)

( * ) Notice: Subject to any disclaimer, the term of this patent is extended or adjusted under 35 U.S.C. 154(b) by 468 days.

(21) Appl. No.: 10/559,229

(22) PCT Filed: Jun. 9, 2004

(86) PCT No.: PCT/CN2004/000621

§ 371 (c)(1),
(2), (4) Date: Dec. 6, 2005

(87) PCT Pub. No.: WO2004/108028

PCT Pub. Date: Dec. 16, 2004

(65) Prior Publication Data

US 2006/0130850 A1 Jun. 22, 2006

(30) Foreign Application Priority Data

Jun. 9, 2003 (CN) ................................. 03 1 29136

(51) Int. Cl.
*A61F 5/56* (2006.01)
*A61C 5/14* (2006.01)
(52) U.S. Cl. .................. 128/848; 128/859; 600/24; 433/6; 602/902
(58) Field of Classification Search ................ 128/848, 128/859–862; 600/23–24; 602/902; 433/6
See application file for complete search history.

(56) References Cited

U.S. PATENT DOCUMENTS

| 4,669,459 | A | * | 6/1987 | Spiewak et al. | ............. | 128/848 |
| D303,834 | S | * | 10/1989 | Collins, Jr. | ................. | D24/180 |
| 4,901,737 | A | * | 2/1990 | Toone | ......................... | 128/848 |
| 5,915,385 | A | * | 6/1999 | Hakimi | ....................... | 128/848 |
| 6,418,933 | B1 | * | 7/2002 | Strong | ......................... | 128/848 |

(Continued)

FOREIGN PATENT DOCUMENTS

CN 2075076 U * 4/1991

(Continued)

*Primary Examiner*—Patricia M Bianco
*Assistant Examiner*—Keri J Nicholson
(74) *Attorney, Agent, or Firm*—Rabin & Berdo, P.C.

(57) ABSTRACT

A comfortable and viable and removable device of channel-type tongue position correction for anti-snoring. The device is made of wire or band material, including a fixer, an upper and nether force-components which are connected with the fixer. The device is mostly applied on upper jaw. The force end of the upper force-component is designed to be suitable to the soft palate palatine velum, and acts to raise up the soft palate palatine velum and uvula upward/upward and backward suitably. The force end of the nether force-component is designed to be suitable to the normal configuration of the corpora linguae (anterior tongue), and acts on the portion in front of the sensitive position of the hind half of the corpora linguae (anterior tongue) to press the big tongue downward/downward and forward. Thus, depending on the co-action of the upper and nether force-components, the blocked respiratory tract could be expanded to prevent snore and remit sleep apnoea syndrome.

16 Claims, 6 Drawing Sheets

U.S. PATENT DOCUMENTS

| | | | |
|---|---|---|---|
| 6,526,982 B1 * | 3/2003 | Strong | 128/848 |
| 6,766,802 B1 * | 7/2004 | Keropian | 128/848 |
| 6,955,172 B2 * | 10/2005 | Nelson et al. | 128/848 |
| 7,073,505 B2 * | 7/2006 | Nelson et al. | 128/848 |
| 7,146,982 B2 * | 12/2006 | Mousselon et al. | 128/848 |
| 7,216,648 B2 * | 5/2007 | Nelson et al. | 128/848 |
| 2001/0027793 A1 * | 10/2001 | Tielemans | 128/848 |
| 2003/0056797 A1 * | 3/2003 | Strong | 128/861 |
| 2004/0045555 A1 * | 3/2004 | Nelson et al. | 128/848 |
| 2004/0045556 A1 * | 3/2004 | Nelson et al. | 128/848 |

FOREIGN PATENT DOCUMENTS

| | | | |
|---|---|---|---|
| DE | 19512761 | * | 10/1996 |
| DE | 20214663 U1 | * | 1/2003 |
| EP | 0679378 | * | 11/1995 |

* cited by examiner

REMOVABLE TONGUE POSITION CORRECTIVE ANTI-SNORING AND ANTI-SUFFOCATING DEVICE

This application is a national phase entry and claims priority from Patent Cooperation Treaty application PCT/CN2004/000621, filed Jul. 9, 2004, which claims priority from Chinese patent application 03129136.8, filed Jun. 9, 2003, the contents of all of which are incorporated herein by reference.

FIELD OF THE INVENTION

The present invention relates to a snore curing field, especially relates to a comfortable and viable and removable device of channel-type tongue position correction for anti-snoring for preventing snore and remitting sleep apnoea syndrome (i.e. the so-called the snoring with suffocating).

BACKGROUND ART

The snore is a rebarbative but very familiar physiological phenomenon, it results in not only affecting other sleeping person in the same or adjacent room, but also an apnoea and even suffocation for short of oxygen, then induces many diseases, harms to health, reduces the efficiency of work and learning and even reduces life-span. The basic reason for snore is an obstructive respiratory tract, people in clinic found that most of the snore is caused by the intra-oral organs (mainly big tongue root and uvula) to block wholly or partially the nasopharyngeal cavity. The intra-oral structure of each people may be slowly deformed along with the increased age, increased fat and flabby muscle etc. The palate and tongue form a natural barrier in the mouth to assist the food swallowing and air transferring, if the palate is gradually drooping and the big tongue is gradually raising, the inner form of oral cavity would be changed to result in blocking the tract, and form a "whistle" effect, the snoring is thus produced. The curing method for snore includes operation, medicine and positive press breath machine assistant and orthopedics method. Among which, the orthopedics method is no traumatic, no side-effect, and simple and convenient, thus has a well development in the future.

The former utility model (90215295) discloses an orthopedics method of NiTi shape memory alloy anti-snoring device, it is made from the NiTi shape memory alloy material to manufacture a force component that suitable to the normal tongue root or soft palate, and acts on the affected part (i.e. the big tongue root and uvula) of patient's body to stop the snoring. FIG. 1 is a schematic show in the prior part of my Chinese patent 9021529.5 (i.e. CN2,075,076). Apart from the plastic base 27 and a clasp 29, it also uses a support bar 28, a force-component 25 and a holding plate 26 embedded in the plastic base 27. As seen in FIG. 1, it is an anti-snoring device designed to suit the mandibles, and one end of the lower force-component 25 is connected with the support bar 28 and embedded with it in the plastic base 27, the other end of the lower force-component 25 bows along the back of the tongue to the tongue's midline, turns to the tongue root, then is embedded in the lower holding plate 26; one end of the upper force-component 25 is also embedded in the lower holding plate 26, the other end of the upper force-component 25 bends in a semicircular arc, takes advantage of the opportunity to extend backwardly and up to the uvula, and then is embedded in the upper holding plate 26. It should be pointed out, however, that this prior technique has the three fatal flaws listed below: (1) it often suffers from the upward pushing force from the big tongue root since it is mostly applied on lower jaw, the pushing force is conducted through clasp to the teeth and will produce some bad pain as pulling out teeth; (2) since it directly acts on the uvula position, but after research people find that the other tissue near the uvula (e.g. tongue palate bow and palate tonsil) is more sensitive and easy to cause itch and nausea; (3) since it acts directly on the big tongue root, and after research we find that the big tongue root itself is specially sensitive and easier to cause pain and nausea. The above three defects prevent it from, the application of the invention, resulted in only about 1-2 of every 100 patients who could be fitted with a limited comforts. Therefore the invention is actually a faulty, impractical and ineffective invention.

SUMMARY OF THE INVENTION

The purpose of the present invention is to overcome the above drawbacks, providing a comfortable and viable and removable device of channel-type tongue position correction for anti-snoring, which indeed makes patients easily adapt and accept it with the ideal anti-snoring and anti-suffocating effects.

The technical scheme of the present invention is as follows: it makes use of wire or band material provided with suitable elasticity and rigidity to manufacture a comfortable and viable and removable device of channel-type tongue position correction for anti-snoring which mostly applied on upper jaw, it includes at least a fixer, an upper force-component and a lower force-component, each end (i.e. non-force end) of the upper and lower force-component is connected with the fixer, the other end (i.e. force end) of the said upper force-component is designed to be suitable to the normal configuration of the soft palate palatine, the head has a support plate and is designed to be located on the portion in front of the sensitive position of the soft palate palatine, it could suitably raise up the palatine and uvula (i.e. "small tongue") upward/upward and backward without causing discomfort and nausea of peripheral tissue; the other end (i.e. force end) of the said lower force-component is designed to be suitable to the normal configuration of the posterior of the tongue, the head has a support plate and is designed to be located on the portion in front of the sensitive position of the posterior of the big tongue, and could press the big tongue downward/downward and forward without causing discomfort and nausea of peripheral tissue. In this way, the blocked respiratory tract could be enlarged, and on the premise of comfort, it works to prevent snoring and remit sleep apnoea syndrome (i.e. the suffocating).

DETAILED DESCRIPTION OF SPECIFIC EMBODIMENTS

In the figures, 1 is the fixer, 2 is the upper force-component, 3 is the lower force-component, 4 is the support plate, 5 is the base support (tongue support/palate support/collar support), 6 is the support bar (lingual bar/palatal bar/cheek bar/labial bar), 7 is the direct fixer (collar/lip bow etc), 8 is the indirect fixer (tongue plate/palate plate/pole etc), 9 is the additional functional part (guide plate/occlusal plate/occlusal pad etc), 10 is the circle fixer (ring/coronet etc), 11 is the link bar, 12 is the connector, 13 is the adjustment, 14 is the teeth, 15 is the clip, 16 is the connecting wire, 17 is the group clips, 18 is the axial clip, 19 is the attachment/magnetic implant, 20 is the complete denture, 21 is the concealed dental prosthesis, 22 is tooth cover, 25 is chen's force component, 26 is chen's holding plate, 27 is chen's plastic base, 28 is chen's support bar, 29 is chen's clasp.

Figure 1:
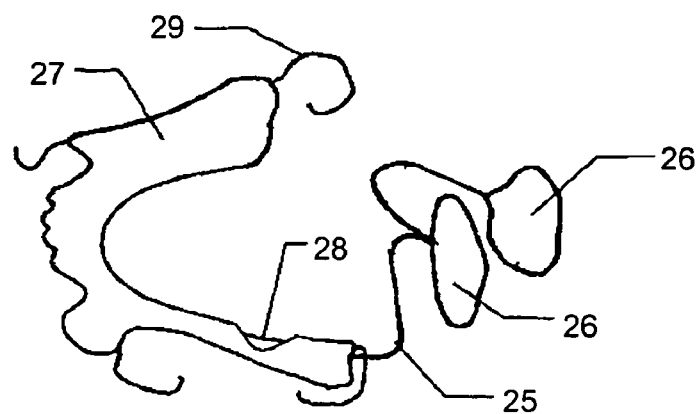
FIG. 1 is an illustrative view showing the NiTi shape memory alloy anti-snoring device of the prior art China patent 90215295.
Figure 2:
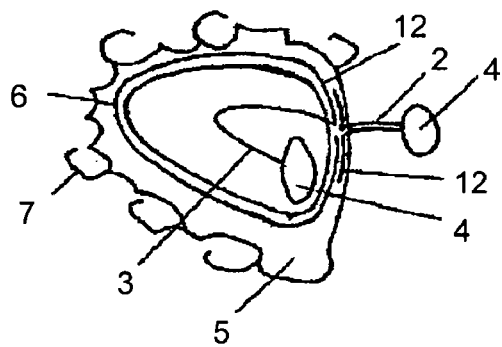
FIG. 2 is an illustrative view showing the 1st embodiment of the comfortable and viable and removable device of channel-type tongue position correction for anti-snoring according to the present invention.

Refer to FIG. 2, the comfortable and viable and removable device of channel-type tongue position correction for anti-snoring according to the present invention is mostly applied on upper jaw, including fixer 1, upper force-component 2 and lower force-component 3, the upper force-component 2 and lower force-component 3 are made of material (preferably high elastic alloy wire or band) provided with suitable elasticity and rigidity. The extension part (i.e. the connector 12) of the non-force end of the upper force-component 2 is embedded in the fixer 1, the other end (i.e. force end) is designed to be suitable to the normal configuration of the soft palate palatine, the head has a support plate 4 and is designed to be located on the portion in front of the sensitive position of the soft palate palatine and little withstand it. Thus, on the premise of not causing discomfort and nausea of peripheral tissue, it could bring an externally reinforced force to the soft palate palatine to prevent snoring. The connector 12 of the non-force end of the lower force-component 3 is also embedded in the fixer 1, but the other end (i.e. force end) is bowed first along the palatine median suture to the anterior lip, then bowed downwardly and backwardly away from the anterior lip, the check side like a bowed nose bridge along the palate, the bottom of bridge is designed to be suitable to the normal configuration of the posterior of the big tongue, the head of the force end of the lower force-component has a support plate 4 and is designed to be located on the portion in front of the sensitive position of the posterior of the big tongue, and press the big tongue downward/downward and forward, thus, on the premise of not causing discomfort and nausea of peripheral tissue, the tongue root is pinned effectively to prevent shrinking backward and closing up the palatine or uvula to cause the pharyngonasal cavity blocking and produce suffocating and snoring, and the co-action of the upper and lower force-components 2,3 could remarkably enlarge and keep the intra-oral effective inner space, thus could increase the breath efficiency and prevent developing sleep apnoea syndrome. The support plate 4 set on the head portion of the force end of the upper and lower force components 2,3 is to divide the force of the force-components 2,3 onto the contact position evenly. The support plate 4 is generally made from synthetic resin (plastic etc) and/or soft polymer material (silicon rubber etc); and its size and shape should be suitable to the position.

In the comfortable and viable and removable device of channel-type tongue position correction for anti-snoring according to the present invention, the fixer 1 may have various forms. As FIG. 2 shows, it is only a normal form, which suitable for snoring patients with good teeth fixing. The fixer includes base support 5 (here is a palatal base), support bar 6 (here is a palatal bar) and direct fixer 7 (collar etc), the whole anti-snoring device is fixed onto the suitable position of the upper jaw of the patient. And the indirect fixer 8 (palate-plate/pole etc) may be used in need to reinforce fixing and safety factor.

Figure 3:
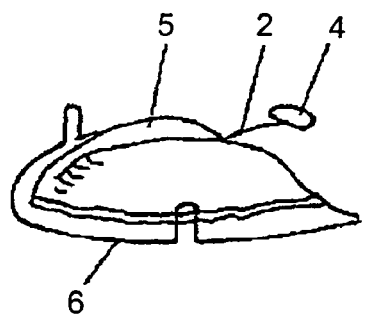
FIG. 3 is an illustrative view showing the 2nd embodiment of the comfortable and viable and removable device of channel-type tongue position correction for anti-snoring according to the present invention.

Refer to FIG. 3, it shows a comfortable and viable and removable device of channel-type tongue position correction for anti-snoring according to the present invention including at least the base support 5 and support bar 6 (here is a labial bar). Its base support may be made of plastic with soft polymer material (silicon rubber etc) covering on it to increase the flexibility with the palate; In terms of need, the palate side may add the support bar 6 (palatal bar) to increase rigidity and/or decrease base support's area; Vertical curve may be set on the labial bar for dismounting. This kind of the anti-snoring device is suitable for the snoring patient with good dentition condition of palate.

Figure 4:
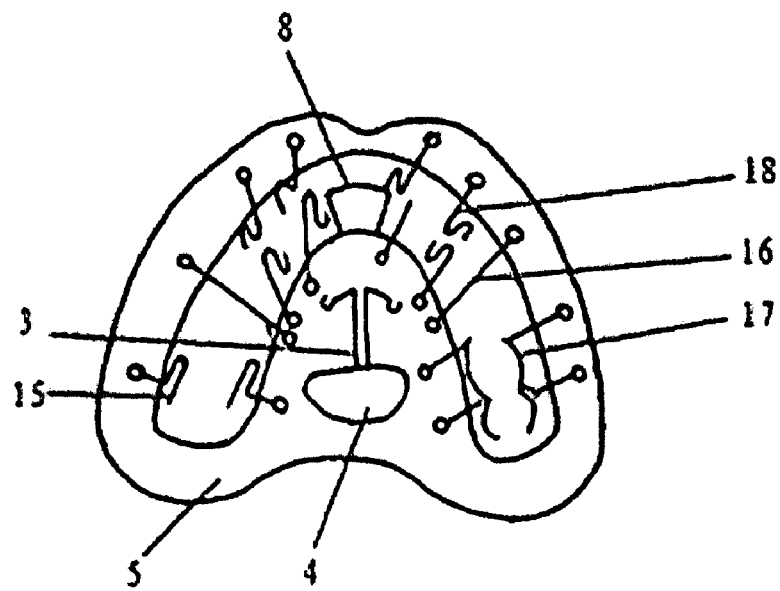
FIG. 4 is an illustrative view showing the 3rd embodiment of the comfortable and viable and removable device of channel-type tongue position correction for anti-snoring according to the present invention.

Refer to FIG. 4, it shows a comfortable and viable and removable device of channel-type tongue position correction for anti-snoring according to the present invention, which includes at least base support 5 (here is a collar support) and direct fixer 7 (here is clip 15, connecting wire 16, group clips 17, axial clip 18 etc). The lip-cheek side and tongue-palate side of the collar support may respectively make use of the partial support bar (labial bar/lingual palatal bar) to increase the rigidity and/or decrease base support's area, an indirect fixer 8 (palate-plate/pole etc) may also be added to reinforce fixing, this kind of the anti-snoring device is suitable for the snoring patient with poor fixing, the force-component 3 is similar to a semi-tube with a seam in middle of it as figure shows.

Figure 5:
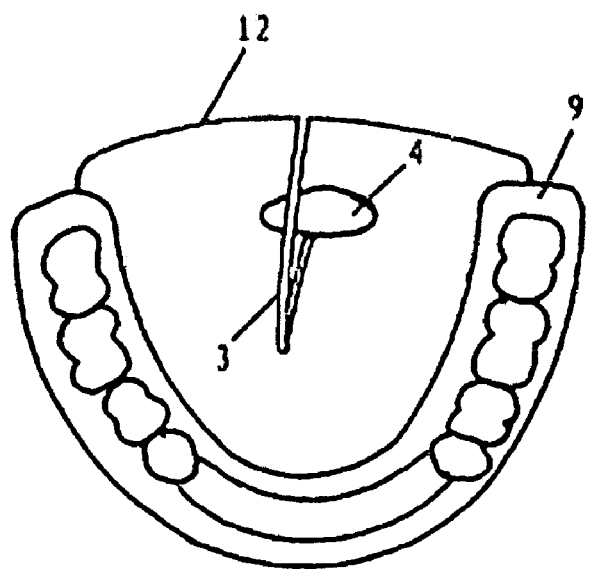
FIG. 5 is an illustrative view showing the 4th embodiment of the comfortable and viable and removable device of channel-type tongue position correction for anti-snoring device according to the present invention.

Refer to FIG. 5, it shows a comfortable and viable and removable device of channel-type tongue position correction for anti-snoring according to the present invention, which uses at least the function accessory 9 (here is an occlusal pad) as the fixer. It requires that the occlusal surface of the occlusal pad should have a deep groove to cover the tooth tip and incisal edge. To increase rigidity, the support bar 6 (lingual palatal bar/labial bar) may be set and the postdam may be closed. This kind of the anti-snoring device is suitable for the snoring patient with good teeth fixing or small occlusal height.

Figure 6:
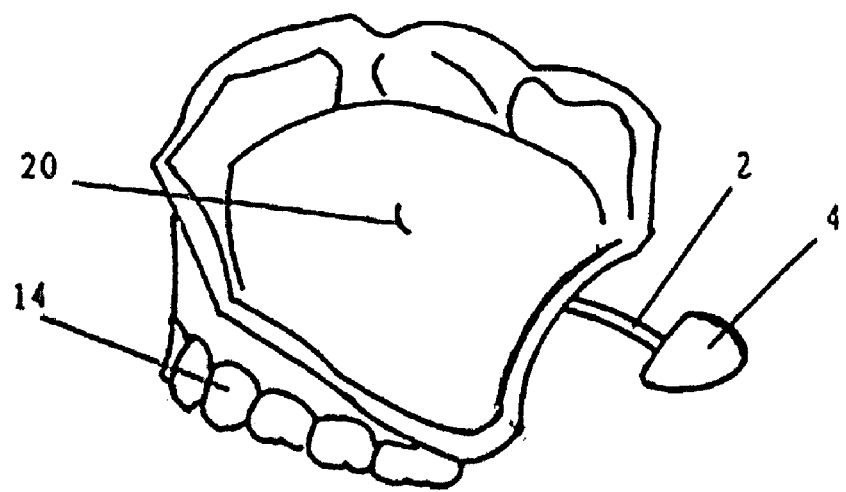
FIG. 6 is an illustrative view showing the 5th embodiment of the comfortable and viable and removable device of channel-type tongue position correction for anti-snoring according to the present invention.

Refer to FIG. 6, it shows a comfortable and viable and removable device of channel-type tongue position correction for anti-snoring according to the present invention which uses at least the complete denture 20 as the fixer. Its tongue-palate side may also be added a support bar (lingual palatal bar) to decrease the base support's area. This kind of the anti-snoring device is suitable for the snoring patient with non dental jaw.

Figure 7:
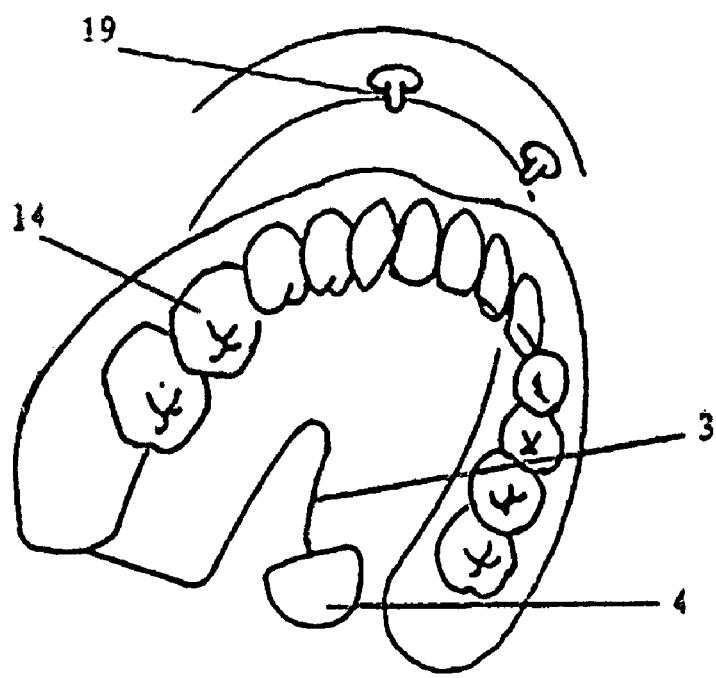
FIG. 7 is an illustrative view showing the 6th embodiment of the comfortable and viable and removable device of channel-type tongue position correction for anti-snoring according to the present invention.

Refer to FIG. 7, it shows a comfortable and viable and removable device of channel-type tongue position correction for anti-snoring according to the present invention which uses at least the coving dental prosthesis or magnetic implant as the fixer, characterized in that it has parts to form a complete set with precision attachment/button circular key or magnetic implant 19. It is suitable for the snoring patient with many bad teeth or high fixing requirement. Its postdam may be closed, and added a support bar 6 (lingual palatal bar etc) or netlike bracket to increase rigidity.

Figure 8:
FIG. 8 is an illustrative view showing the 7th embodiment of the comfortable and viable and removable device of channel-type tongue position correction for anti-snoring according to the present invention.

Refer to FIG. 8, it shows a comfortable and viable and removable device of channel-type tongue position correction for anti-snoring according to the present invention which uses at least the concealed dental prosthesis as the fixer. A base support (plastic) may be set on the tongue palate side to increase rigidity and embed the support bar (lingual palatal bar etc), and its postdam may be closed. This kind of the anti-snoring device is suitable for the snoring patient with non dental jaw and less teeth of high quality requirement.

Figure 9:
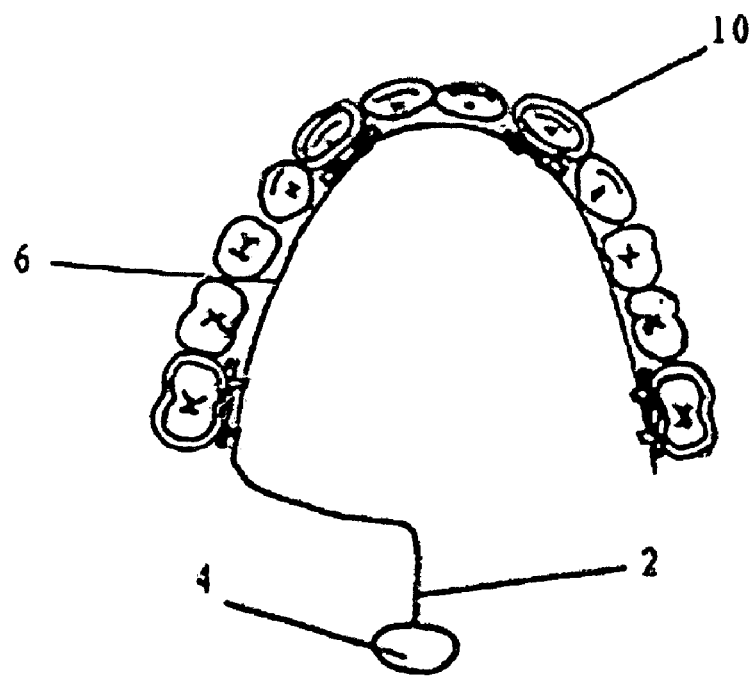
FIG. 9 is an illustrative view showing the 8th embodiment of the comfortable and viable and removable device of channel-type tongue position correction for anti-snoring according to the present invention.

Refer to FIG. 9, it shows a comfortable and viable and removable device of channel-type tongue position correction for anti-snoring according to the present invention which uses at least the support bar 6 (here is a lingual palatal bar) and circle fixer 10 (ring/coronet etc) as the fixer. The non-force end of the force-component is connected with the circle fixer 10 in a suitable way. This kind of the anti-snoring device is suitable for the snoring patient with good dental arch and teeth gap.

Figure 10:
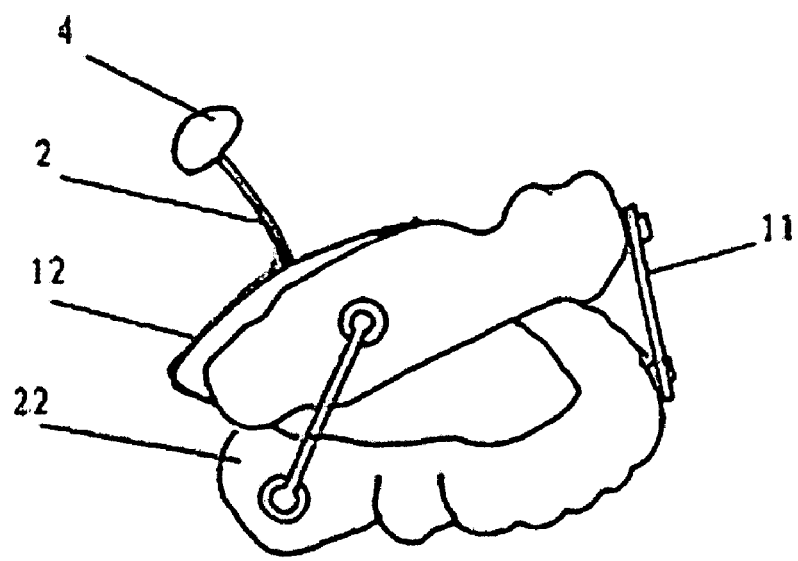
FIG. 10 is an illustrative view showing the 9th embodiment of the comfortable and viable and removable device of channel-type tongue position correction for anti-snoring according to the present invention.

Refer to FIG. 10, it shows a comfortable and viable and removable device of channel-type tongue position correction for anti-snoring according to the present invention which uses at least the tooth cover 22 of the upper and lower jaws and cheek side link bar 11 as the fixer. A base support (plastic) may be set on the tongue palate side, and the support bar (lingual palatal bar) may be embedded in the plastic base support. This kind of the anti-snoring device is suitable for the snoring patient with the shrinking backward of the lower jaw plus abnormal tongue position.

Figure 11:
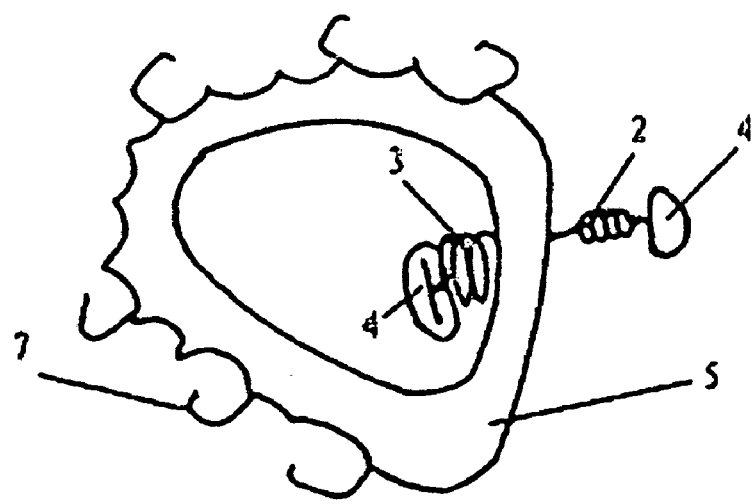
FIG. 11 is an illustrative view showing the 10th embodiment of the comfortable and viable and removable device of channel-type tongue position correction for anti-snoring according to the present invention.
Figure 12:
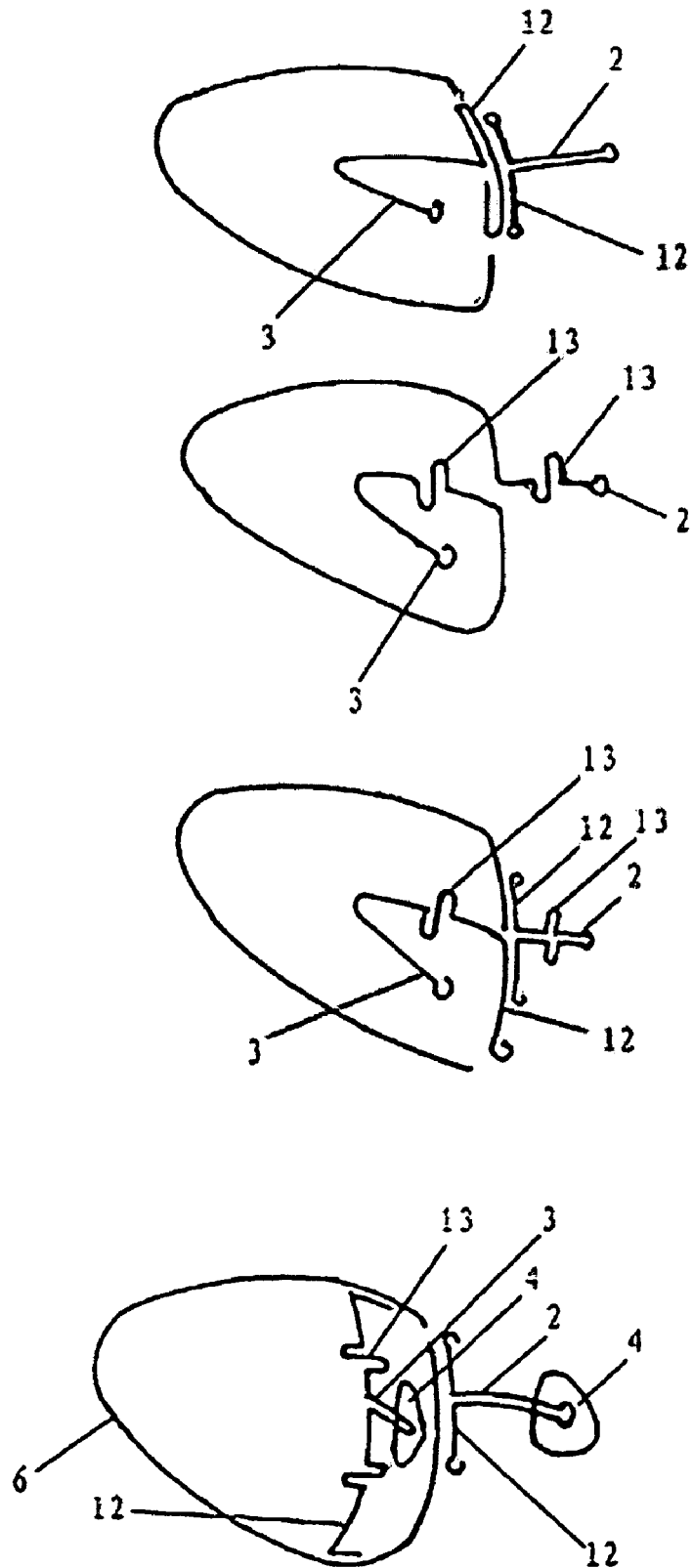
FIG. 12 is an illustrative view showing the 11th embodiment of the comfortable and viable and removable device of channel-type tongue position correction for anti-snoring according to the present invention.

It should notice that, the upper force-component 2 and lower force-component 3 are the most special parts of the anti-snoring device, enough elasticity and suitable rigidity are both extremely important, any one of which is indispensable. Meanwhile, the suitable thickness or diameter is important also, it may directly affect the elasticity. In design, the force-components 2,3 may be connected with the support bar 6, or separated as FIG. 12 shows; it may use same material and size or different material and size. The force end of the force-component 3 may point directly to the end position in form of spring, single wire and band or spring tube (as FIG. 11 and FIG. 4 shows), or indirectly to the end position (as FIG. 5 and FIG. 8 shows); The middle of the force-components 2,3 may at least have an adjustment 13 to adjust the length and angle as FIG. 12 shows. Meanwhile, the support bar 6 may be a lingual bar, palatal bar, cheek bar, labial bar etc; the direct fixer 7 may be a clip and lip bow etc; the indirect fixer 8 may be a lingual plate, palate-plate, pole etc; the function accessory 9 may be a guide plate, occlusal plate or occlusal pad etc.

The above-mentioned comfortable and viable and removable device of channel-type tongue position correction for anti-snoring device above has a good clinic effect and a better design result, it has wider applicable range and a better effect for more than 98% from 100 patients.

Although various exemplary embodiments of the invention have been disclosed, it should be apparent to those skilled in the art that various changes and modifications can be made which will achieve some of the advantage of the invention without departing from the true scope of the invention.

What is claimed is:

1. A comfortable and viable and removable device of channel-type tongue position correction for anti-snoring, comprising:
   a fixer;
   an upper force-component connected with the fixer, and having a force end; and
   a lower force-component connected with the fixer, and having a force end,
   wherein:
   the fixer is located at an upper jaw of a user, or at both the upper jaw and a lower jaw of the user;
   the force end of the upper force-component is designed to be suitable to a normal configuration of a soft palate palatine of the user, the force end of the upper force-component having a support plate, the support plate being designed to be located on a portion in front of a sensitive position of the soft palate palatine, allowing the support plate to suitably raise up the soft palate palatine and an uvula of the user upward/upward and backward without causing discomfort and nausea to a peripheral tissue of the user;
   the force end of the lower force-component is designed to be suitable to a normal configuration of a posterior of a big tongue of the user, the force end of the lower force-component having a support plate, the support plate being designed to be located on the portion in front of a sensitive position of the posterior of the tongue, allowing the support plate to press the big tongue downward/downward and forward without causing discomfort and nausea of peripheral tissue; and
   the upper and lower force-components are made of elastic and rigid material with a gap between them to enlarge an inner space of oral inner space to increase the efficiency of the user's breath, and
   wherein the lower force-component extends from the fixer in a forward direction, and is designed to bow first along the user's palatine median suture to the user's anterior lip, then bow downwardly and backwardly away from the anterior lip, so that the lower force-component forms a nose-like protuberance having at least one bend seen from a user's cheek side, with an appropriate space between the upside and the bottom of the nose-like protuberance.

2. The device according to claim 1, wherein the upper force-component and/or lower force-component are made of wire or band material with suitable thickness or diameter.

3. The device according to claim 2, wherein the upper force-component and/or lower force-component are made of elastic wire and/or band.

4. The device according to claim 1, wherein the support plate has a suitable shape and size and is made from synthetic resin and/or soft polymer material.

5. The device according to claim 1, wherein the fixer includes any one or more of a base support and a support bar, and the fixer is comprised of any one or more of synthetic resin, metal, soft polymer material, concealed dental prosthesis material.

6. The device according to claim 5, wherein:
the denture base support is a tongue support or a palate support or a collar support;
the support bar is a palatal bar, a lingual bar, a labial bar or a cheek bar.

7. The device according to claim 5, wherein the synthetic resin is plastic or white latex, and the soft polymer material is silicone rubber.

8. The device according to claim 1, wherein the fixer is a covering dental prosthesis or a tooth cover or a magnetic implant dental prosthesis.

9. The device according to claim 1, wherein the fixer includes, at its side facing a cheek of the user, a link bar that is capable of moving the jaws in case of setting the fixer on the upper and lower jaws simultaneously.

10. The device according to claim 1, wherein the upper and lower force-components have an adjustment at their respective middle portions to adjust the length and angle in clinic.

11. The device according to claim 1, wherein the upper force-component and/or lower force-component are at least made of single wire or single band material.

12. The device according to claim 11, wherein the upper force-component and/or lower force-component are made of elastic wire and/or band.

13. The device according to claim 1, wherein the upper and lower force-components have an adjustment at their respective middle portions to adjust the length and angle in clinic.

14. The device according to claim 1, wherein the fixer includes a link bar and a circle fixer connected with the link bar, and the circle fixer is a ring or a a coronet.

15. The device according to claim 1, wherein:
the upper force-component has a non-force end that is embedded in the fixer;
if the final position of the support plate of the upper force-component is regarded as a target location, from the vertical view of the anti-snoring device, the upper force-component points directly to the target location from its non-force end; and
if the final position of the support plate of the lower force-component is regarded as a target location, from the vertical view of the anti-snoring device, the lower force-component points directly to the target location from its non-force end.

16. The device according to claim 15, wherein:
the lower force-component has a non-force end that is embedded in the fixer, the non-force end of the lower force-component is separated from the non-force end of the upper force-component;
if the final position of the force end of the upper force-component is regarded as a target location, from the vertical view of the anti-snoring device, the upper force-component points directly to the target location from the fixer toward a first direction; and/or
if the final position of the force end of the lower force-component is regarded as a target location, from the vertical view of the anti-snoring device, the lower force-component points directly to the target location from the fixer toward a second direction opposite to the first direction.

\* \* \* \* \*